(12) United States Patent
Wang et al.

(10) Patent No.: US 10,939,945 B2
(45) Date of Patent: Mar. 9, 2021

(54) MINIMALLY INVASIVE BONE FRACTURE POSITIONING DEVICE

(71) Applicant: METAL INDUSTRIES RESEARCH & DEVELOPMENT CENTRE, Kaohsiung (TW)

(72) Inventors: Yue-Jun Wang, Kaohsiung (TW); Chih-Hao Chang, Kaohsiung (TW); Shih-Hua Huang, Kaohsiung (TW); Chih-Lung Lin, Kaohsiung (TW); Tung-Lin Tsai, Kaohsiung (TW); Chun-Chieh Tseng, Kaohsiung (TW); Li-Wen Weng, Kaohsiung (TW)

(73) Assignee: METAL INDUSTRIES RESEARCH & DEVELOPMENT CENTRE, Kaohsiung (TW)

( * ) Notice: Subject to any disclaimer, the term of this patent is extended or adjusted under 35 U.S.C. 154(b) by 513 days.

(21) Appl. No.: 15/814,488

(22) Filed: Nov. 16, 2017

(65) Prior Publication Data
US 2019/0142488 A1 May 16, 2019

(51) Int. Cl.
| | |
|---|---|
| *A61B 17/88* | (2006.01) |
| *A61B 17/64* | (2006.01) |
| *A61B 17/17* | (2006.01) |
| *A61B 17/66* | (2006.01) |
| *A61B 17/68* | (2006.01) |

(52) U.S. Cl.
CPC ...... *A61B 17/8866* (2013.01); *A61B 17/1782* (2016.11); *A61B 17/6408* (2013.01); *A61B 17/8872* (2013.01); *A61B 17/6416* (2013.01); *A61B 17/6466* (2013.01); *A61B 17/66* (2013.01); *A61B 2017/681* (2013.01)

(58) Field of Classification Search
CPC ............ A61B 17/6408; A61B 17/6433; A61B 17/6466; A61B 17/8866; A61B 17/8872; A61B 17/1782
See application file for complete search history.

(56) References Cited

U.S. PATENT DOCUMENTS

| | | | | |
|---|---|---|---|---|
| 5,163,940 | A * | 11/1992 | Bourque | A61B 17/1714 606/103 |
| 5,437,667 | A * | 8/1995 | Papierski | A61B 17/6425 606/55 |
| 7,316,687 | B2 * | 1/2008 | Aikins | A61B 17/1668 606/70 |

(Continued)

FOREIGN PATENT DOCUMENTS

| | | |
|---|---|---|
| CN | 205514869 U | 8/2016 |
| CN | 205903304 U | 1/2017 |
| TW | I257457 B | 7/2006 |

*Primary Examiner* — Anu Ramana
(74) *Attorney, Agent, or Firm* — Alan D. Kamrath; Karin L. Williams; Mayer & Williams PC

(57) ABSTRACT

A minimally invasive bone fracture positioning device includes a sleeve, a movable unit, and a support. The sleeve includes an alignment portion located on a longitudinal axis of the sleeve. The movable unit includes a positioning portion. The positioning portion is located on the longitudinal axis and is spaced from the alignment portion. The movable unit is mounted in a radial direction of the sleeve. The movable unit is slideable relative to the sleeve along the longitudinal axis. A support is coupled to the sleeve and the movable unit. The movable unit is spaced from the sleeve by the support.

11 Claims, 5 Drawing Sheets

(56) References Cited

U.S. PATENT DOCUMENTS

| | | | | |
|---|---|---|---|---|
| 7,481,815 B2 * | 1/2009 | Fernandez | ......... | A61B 17/1703 |
| | | | | 606/97 |
| 8,142,432 B2 * | 3/2012 | Matityahu | .......... | A61B 17/1728 |
| | | | | 606/54 |
| 2002/0151897 A1 * | 10/2002 | Zirkle, Jr. | .......... | A61B 17/1725 |
| | | | | 606/62 |
| 2005/0222575 A1 * | 10/2005 | Ciccone | ............. | A61B 17/1615 |
| | | | | 606/104 |
| 2014/0163623 A1 * | 6/2014 | Humphrey | ......... | A61B 17/1728 |
| | | | | 606/291 |
| 2014/0249536 A1 * | 9/2014 | Jajeh | ................. | A61B 17/1725 |
| | | | | 606/96 |

* cited by examiner

MINIMALLY INVASIVE BONE FRACTURE POSITIONING DEVICE

BACKGROUND

1. Technical Field

The present invention relates to a minimally invasive bone fracture positioning device and, more particularly, to a minimally invasive bone fracture positioning device that can be used through two small open wounds.

2. Description of the Related Art

When a bone has a serious fracture misalignment problem, it is necessary to implant a bone nail through an operation to assure reliable engagement of the fracture during the recovery period after accurate osteosynthesis. During a surgery including drilling a hole and implanting a bone nail, a bone fracture positioning device is firstly used to tightly clamp two ends of the fractured part of the bone to assure that the bone remains tight and accurate joining at the fracture while providing positioning and orientation functions to assist in the therapy.

However, two ends of the above conventional bone fracture positioning device for clamping and positioning are coaxially moved and, thus, require incision of a skin in the fracture joining direction to form a large open wound for insertion of the bone fracture positioning device whose two ends can, thus, be used to precisely clamp the bone. The vessels and nerves surrounding the bone must be handled during the surgery, and the fracture extending direction decides practice of a straightforward surgery or an inverse surgery whose route encounters vessels and nerves in different positions from those in the straightforward surgery. Thus, the complication and the operation time of the surgery will be increased, affecting the post-surgery recovery conditions and increasing the burden of the body of the patient.

Thus, improvement to the conventional bone fracture positioning devices is necessary.

SUMMARY

To solve the above problems, an objective of the present invention is to provide a minimally invasive bone fracture positioning device that can proceed with positioning of a broken bone in a surgery during which only two small open wounds are required, reducing the operation risk and the burden to the body of the patient.

Another objective of the present invention is to provide a minimally invasive bone fracture positioning device capable of providing various combinations of different components in response to various fractures patterns in different locations, providing versatile applications according to operation needs while reducing the inventory pressure of apparatuses of different specifications.

When the terms "front", "rear", "left", "right", "up", "down", "top", "bottom", "inner", "outer", "side", and similar terms are used herein, it should be understood that these terms have reference only to the structure shown in the drawings as it would appear to a person viewing the drawings and are utilized only to facilitate describing the invention, rather than restricting the invention.

A minimally invasive bone fracture positioning device according to the present invention includes a sleeve, a movable unit, and a support. The sleeve includes an alignment portion located on a longitudinal axis of the sleeve. The movable unit includes a positioning portion. The positioning portion is located on the longitudinal axis and is spaced from the alignment portion. The movable unit is mounted in a radial direction of the sleeve. The movable unit is slideable relative to the sleeve along the longitudinal axis. A support is coupled to the sleeve and the movable unit. The movable unit is spaced from the sleeve by the support.

Thus, in the minimally invasive bone fracture positioning device according to the present invention, the alignment portion and the positioning portion having a pressing distance therebetween can be used to proceed with positioning during therapeutic steps such as drilling a hole and implanting the bone nail while only requiring two small open wounds. This avoids undesired risks of straightforward and inverse surgeries and reduces the burden to the body of the patient in the subsequent recovery period. Furthermore, various combinations of different fixing hooks and different sleeves can be used according to different fracture patterns in different locations, providing versatile applications according to the operation needs while reducing the inventory pressure of apparatuses of different specifications.

In an example, the minimally invasive bone fracture positioning device further includes an operating rod extending through the sleeve, and the operating rod includes a front end extending out of the sleeve via the alignment portion. This increases the precision and stability of the surgery.

In an example, a drilling member is removably mounted to the front end of the operating rod. A hole can be drilled in the broken bone in a determined direction.

In an example, a bone nail is removably mounted to the front end of the operating rod. The bone nail can be implanted into the broken bone.

In an example, the movable unit includes a block fixed to the support and a track, and the block is slideably mounted to the track. Thus, the movable unit can slide relative to the block and the support.

In an example, the block includes a track groove extending along the longitudinal axis and having a lateral opening. The track is slideably received in the track groove. A cover is mounted to the block to cover the lateral opening. The cover prevents the track from disengaging from the track groove.

In an example, the track includes a first side having a first guiding groove and a second side spaced from the first side in a lateral direction perpendicular to the longitudinal axis and having a second guiding groove. Thus, the track can slide stably.

In an example, the block includes a first protrusion slideably received in the first guiding groove, and the cover includes a second protrusion slideably received in the second guiding groove. Thus, the track can slide smoothly relative to the block and the cover.

In an example, a fixing hook is fixed to an end of the track, and the positioning portion is disposed on a distal end of the fixing hook. Thus, tissues surrounding the broken bone can be avoided while assisting in positioning of the fracture of the broken bone.

In an example, the fixing hook is C-shaped, G-shaped, J-shaped, L-shaped, or U-shaped, and the positioning portion is in a form of a hook, a claw, or a collar. A desired fixing hook can be selected to match with the position, length, and fracture extending direction of the broken bone, providing convenient options for a doctor.

In an example, the track includes a measurement portion in the form of a scale on a surface of the track. The displacement of the track can be known by the measurement portion and can be converted into the distance between the alignment portion and the positioning portion. Thus, the depth of the hole to be drilled in the broken bone and the size of the bone nail can be selected.

In an example, the block includes a first engaging portion, the support includes a second engaging portion, and the first engaging portion and the second engaging portion have correspondingly formed engagement grooves. Thus, the block can be conveniently and reliably fixed to the support.

The present invention will become clearer in light of the following detailed description of illustrative embodiments of this invention described in connection with the drawings.

DETAILED DESCRIPTION

Figure 1:
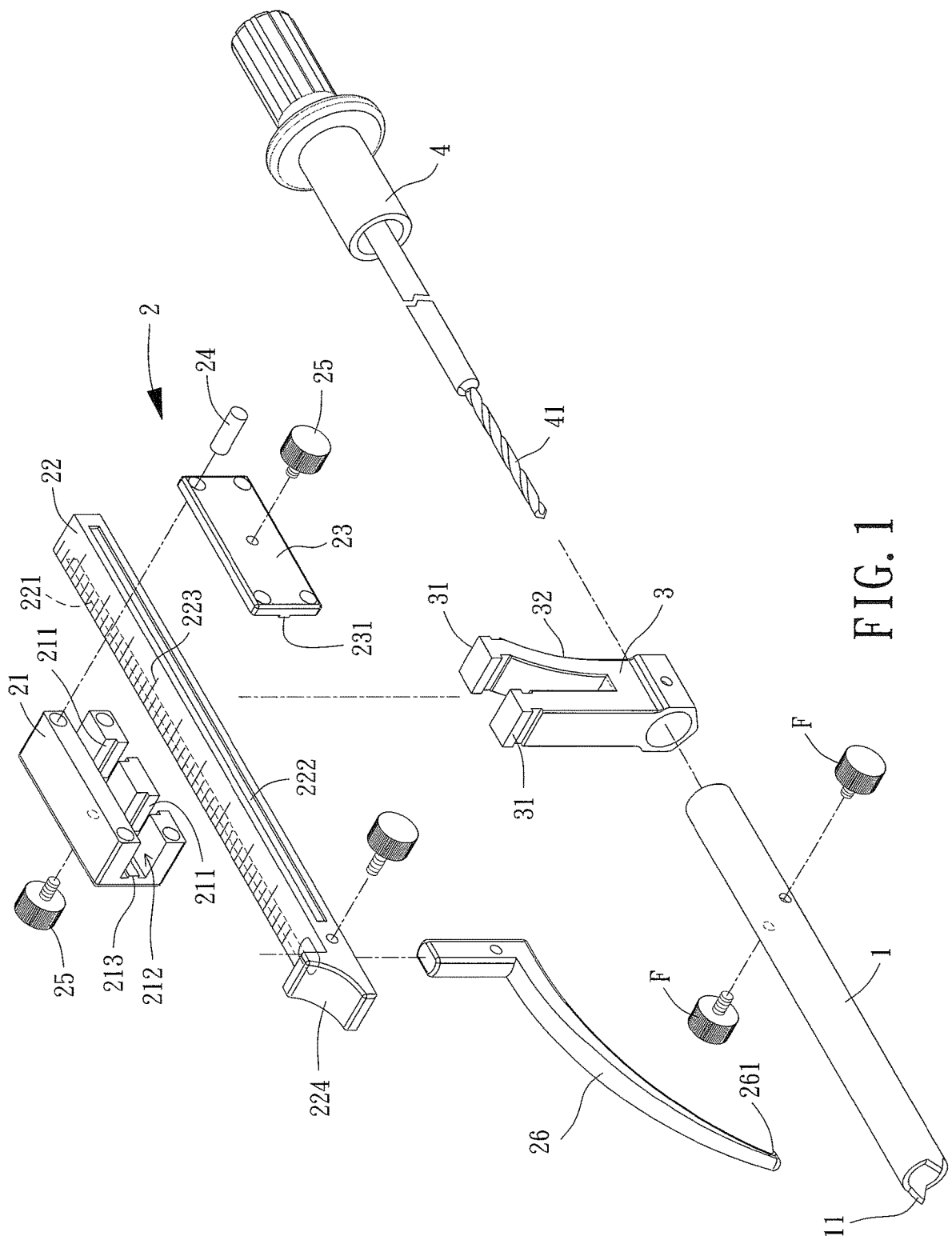
FIG. 1 is an exploded, perspective view of a minimally invasive bone fracture positioning device of an embodiment according to the present invention.
Figure 2:
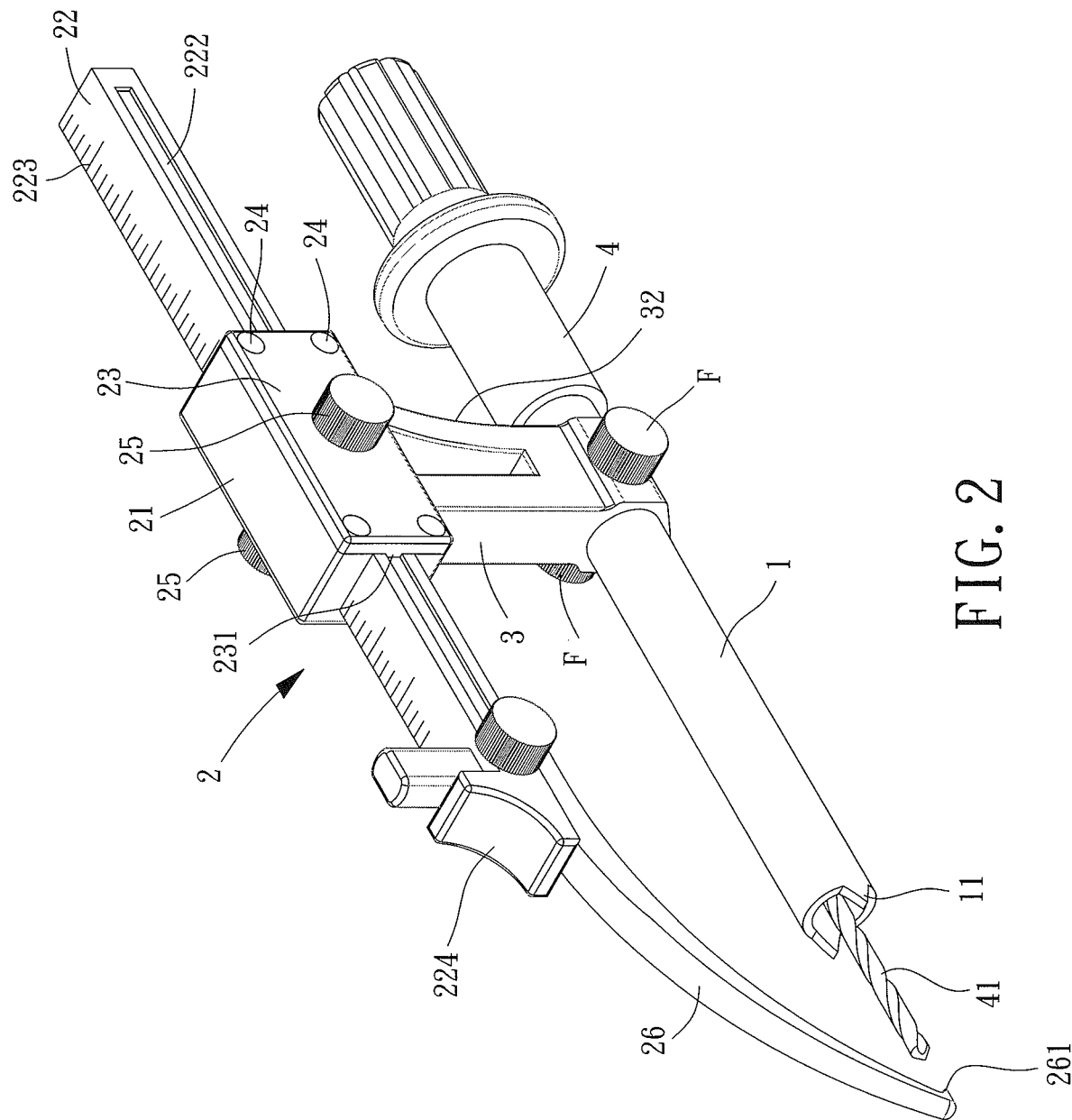
FIG. 2 is a perspective view of the minimally invasive bone fracture positioning device of FIG. 1 after assembly.

With reference to FIGS. 1 and 2, a minimally invasive bone fracture positioning device according to the present invention includes a sleeve 1, a movable unit 2, and a support 3. The support 3 is coupled to the sleeve 1 and the movable unit 2, such that the sleeve 1 is spaced from and parallel to the movable unit 2 by the support 3.

The sleeve 1 includes an alignment portion 11 at an end thereof and located on a longitudinal axis X of the sleeve 1. The alignment portion 11 can be a fixing member in the form of a hook, a claw, or a collar for mating with a shape of a surface of a bone. A therapeutic tool can be inserted into the sleeve 1 via the other end of the sleeve 1.

The movable unit 2 includes a block 21 having a first engaging portion 211 fixed to the support 3 and a track 22. The block 21 is slideably mounted to the track 22. In the embodiment shown, the block 21 includes a track groove 212 extending along the longitudinal axis X for slideably receiving the track 22. After the track 22 is mounted in the track groove 212, a cover 23 is mounted to the block 21 to cover a lateral opening of the block 21 to prevent the track 22 from disengaging from the track groove 212. The cover 23 can be fixed to the block 21 by a plurality of fixing members 24. In the embodiment shown, the track 22 includes a first side having a first guiding groove 221 and a second side spaced from the first side in a lateral direction perpendicular to the longitudinal axis X and having a second guiding groove 222. The block 21 includes a first protrusion 213 slideably received in the first guiding groove 221, and the cover 23 includes a second protrusion 231 slideably received in the second guiding groove 222. Thus, the track 22 can slide smoothly relative to the block 21 and the cover 23. After the track 22 has reached a desired position, the track 22 can be fixed in relation to the block 21. In this embodiment, a fastener 25 extends through the block 21 and can be rotated to a position pressing against a bottom wall of the first guiding groove 221 of the track 22 to retain the track 22 in place. Another fastener 25 extends through the cover 23 and can be rotated to a position pressing against a bottom wall of the second guiding groove 222 of the track 22 to retain the track 22 in place. Each of the fasteners 25 can be in the form of a threaded member. Thus, the track 22 can be retained in a desired location relative to the block 21.

The track 22 can have a measurement portion 223 in the form of a scale or a displacement meter. In this embodiment, the measurement portion 223 is in the form of a scale on a surface of the track 22. Furthermore, a fixing hook 26 is fixed to an end of the track 22. The fixing hook 26 can be a workpiece bent to form a desired shape, such as C-shaped, G-shaped, J-shaped, L-shaped, or U-shaped, for matching with the position, length, and fracture extending direction of the broken bone, which provides convenient options for a doctor or a medical worker. A positioning portion 261 is disposed on a distal end of the fixing hook 26 and can be a fixing member in the form of a hook, a claw, or a collar for mating with a shape of a surface of a bone. In this embodiment, the movable unit 2 is mounted in a radial direction of the sleeve 1 perpendicular to the longitudinal axis C, and the positioning portion 261 is located on the longitudinal axis X and is spaced from the alignment portion 11. An arcuate concave face 224 can be provided on an end of the track 22 (to which the fixing hook 26 is mounted) for easy gripping while serving as a point of application of force.

The support 3 can be integrally formed with or detachably mounted to the sleeve 1. In this embodiment, the support 3 is fixed to the sleeve 1 by fasteners F. The first engaging portion 211 of the movable unit 2 is fixed to a second engaging portion 31 of the support 3. In this embodiment, the first engaging portion 211 and the second engaging portion 31 have correspondingly formed engagement grooves. An arcuate concave face 32 can be provided on an outer side of the support 3 for easy gripping while serving as a point of application of force.

The minimally invasive bone fracture positioning device can further include an operating rod 4 extending through the sleeve 1. A drilling member 41 is removably mounted to a front end of the operating rod 4. The drilling member 41 can be a conventional bit fixed or detachably mounted to the front end of the operating rod 4. The operating rod 4 extends out of the sleeve 1 via the alignment portion 11. A power element (not shown) can be provided to drive the drilling member 41 to rotate.

According to the above structure, the track 22 can slide relative to the block 21 along the longitudinal axis X. Thus, the fixing hook 26 moves relative to the sleeve 1 to adjust the spacing between the alignment portion 11 and the positioning portion 261. When the track 22 is fixed to the block 21, the location of the block 21 in relation to the measurement portion 223 of the track 22 indicates the spacing between the alignment portion 11 and the positioning portion 261 by the marking on the measurement portion 223.

Figure 3:
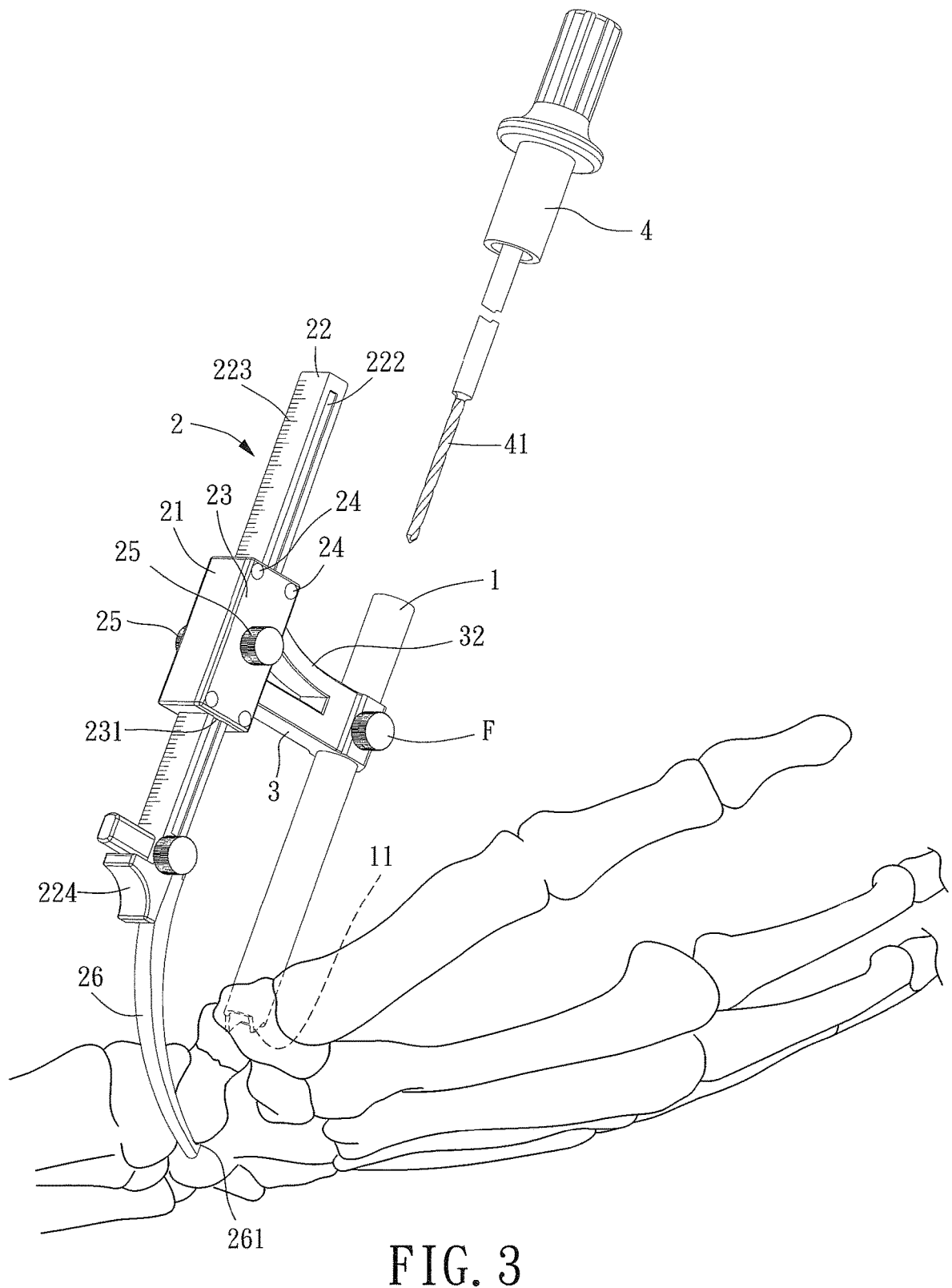
FIG. 3 is a diagrammatic view illustrating use of the minimally invasive bone fracture positioning device of FIG. 2.

With reference to FIG. 3, in use of the minimally invasive bone fracture positioning device, a doctor or a medical worker selects a proper sleeve 1 and a proper fixing hook 26 before surgery, with the sleeve 1 and the fixing hook 26 matching with the angle and location of the drilling operation and the implantation operation for treating a bone fracture. The doctor or the medical worker opens two small open wounds in a body of a patient having a broken bone B, thereby revealing two ends of the broken bone B. During the surgery, the positioning portion 261 of the fixing hook 26 is used to tightly press a positioning point of the broken bone B via one of the two small open wounds, and the alignment portion 11 of the sleeve 1 is aligned with the positioning portion 261 in a positioning direction of the broken bone B. Then, the sleeve 1 and the block 21 are moved relative to the track 22 until the alignment portion 11 of the sleeve 1 tightly abuts another positioning point of the broken bone B via the other small open wound. The alignment portion 11 and the positioning portion 261 can apply forces to the broken bone B via the two positioning points, and the track 22 is fixed to the block 21 by the fasteners 25. Thus, a pressing distance L is maintained between the alignment portion 11 and the positioning portion 261.

Figure 4:
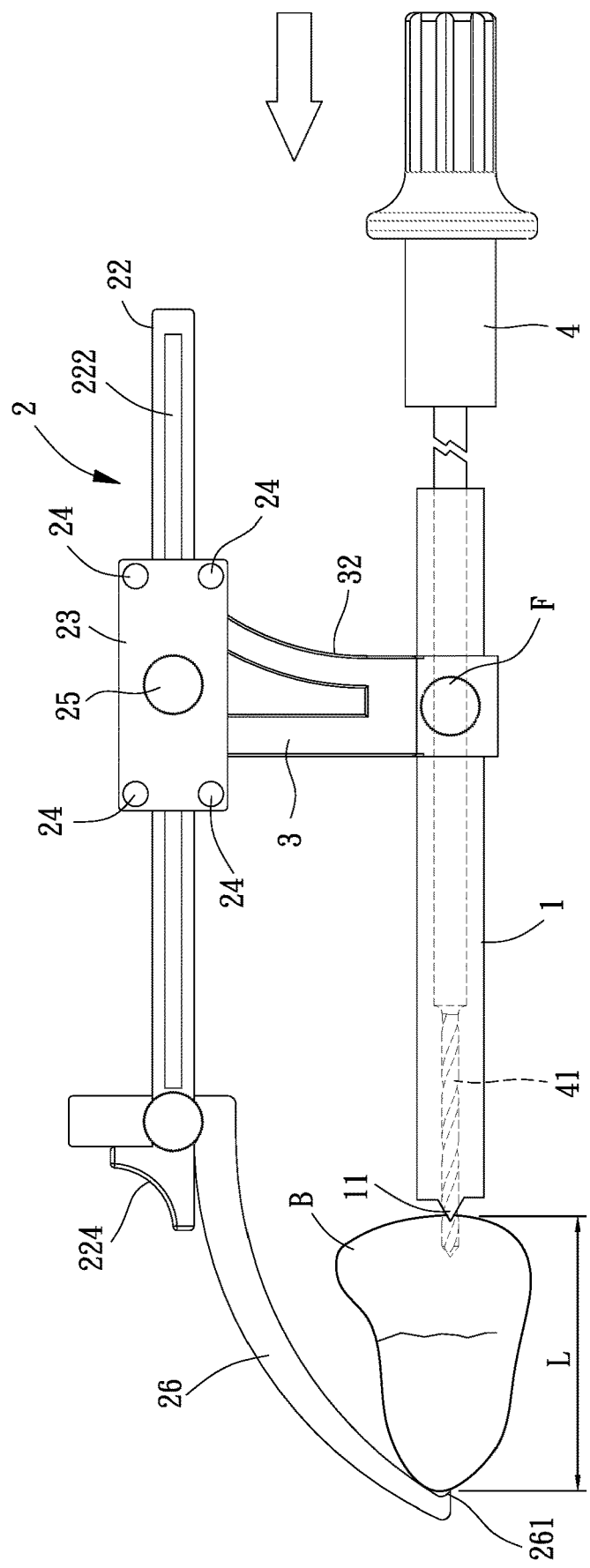
FIG. 4 is a diagrammatic side view illustrating a drilling procedure of the minimally invasive bone fracture positioning device of FIG. 2.

With reference to FIG. 4, after the fracture of the broken bone B has been stably closed, the drilling member 41 of the operating rod 4 is moved forward to extend out of the alignment portion 11 of the sleeve 1, and the power element (not shown) is operated to drive the drilling member 41 to thereby drill a hole in the broken bone B. The measurement portion 223 measures the pressing distance L to judge the depth of the hole in the broken bone B. The alignment portion 11 and the positioning portion 261 maintain the pressing distance L therebetween and continuously and tightly clamp the broken bone B during the drilling procedure, avoiding misalignment of the fracture of the broken bone B.

Figure 5:
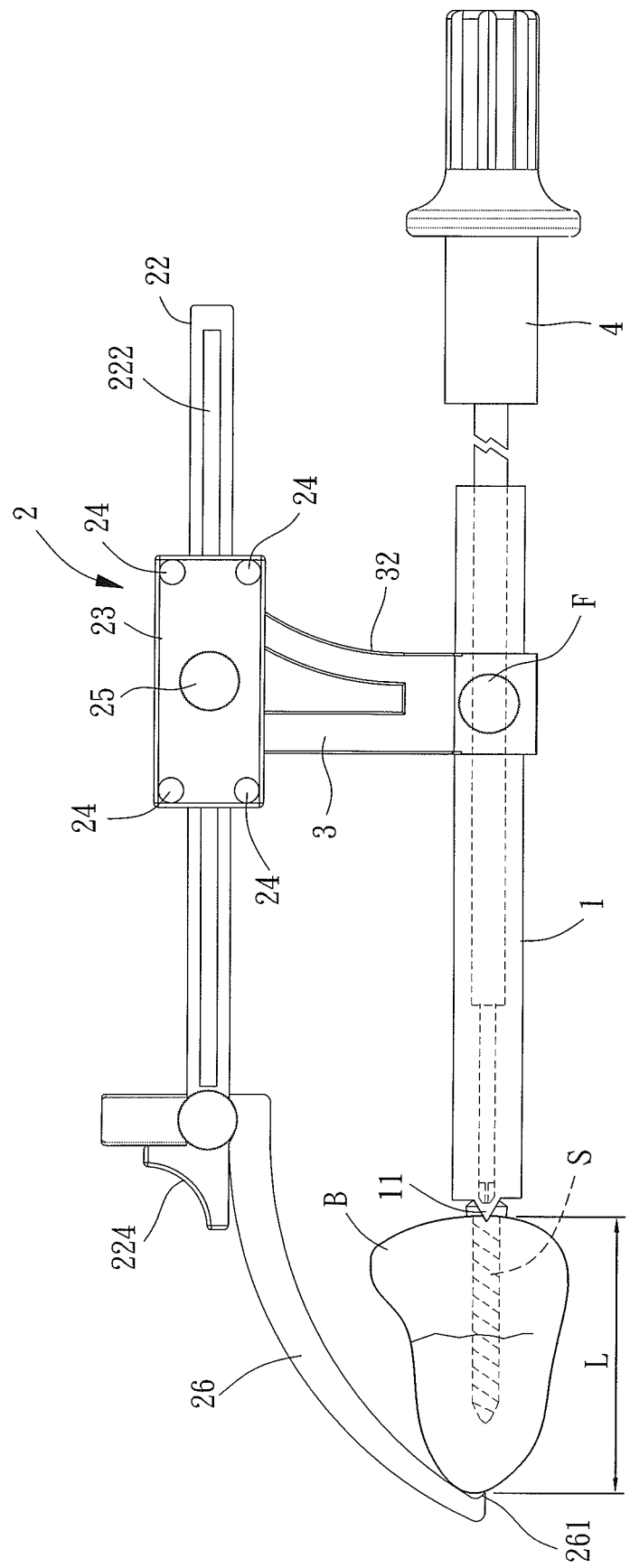
FIG. 5 is a diagrammatic side view illustrating implantation of a bone nail by the minimally invasive bone fracture positioning device of FIG. 2.

With reference to FIG. 5, after drilling, the alignment portion 11 and the positioning portion 261 are not moved, and the operating rod 4 and the drilling member 41 are moved out of the sleeve 1. Next, the drilling member 41 is replaced by a bone nail S, and the bone nail S is pushed and implanted into the broken bone B by the operating rod 4. The bone nail S can close and fix the fracture of the broken bone B. Then, the fasteners 25 are loosened to release the alignment portion 11 and the positioning portion 261 from the broken bone B, and the minimally invasive bone fracture positioning device according to the present invention can be detached subsequently.

In view of the foregoing, in the minimally invasive bone fracture positioning device according to the present invention, the alignment portion 11 and the positioning portion 261 having the pressing distance L therebetween can be used to proceed with positioning during therapeutic steps such as drilling a hole and implanting the bone nail S while only requiring two small open wounds. This avoids undesired risks of straightforward and inverse surgeries and reduces the burden to the body of the patient in the subsequent recovery period. Furthermore, various combinations of different fixing hooks 26 and different sleeves 1 can be used according to different fracture patterns in different locations, providing versatile applications according to the operation needs while reducing the inventory pressure of apparatuses of different specifications.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalency of the claims are intended to be embraced therein.

What is claimed is:

1. A minimally invasive bone fracture positioning device comprising:
    a sleeve including an alignment portion at an end of the sleeve;
    a movable unit including a positioning portion axially opposing to and spaced from the alignment portion of the sleeve, wherein the alignment portion of the sleeve and the positioning portion of the movable unit are configured to respectively hold two ends of a broken bone, wherein the movable unit is radially spaced from the sleeve and is slideable relative to the sleeve along a longitudinal axis of the sleeve; and
    a support coupled to the sleeve and the movable unit, wherein the movable unit is spaced from the sleeve by the support,
    wherein the movable unit includes a block fixed to the support and a track, and wherein the block is slideably mounted to the track.

2. The minimally invasive bone fracture positioning device as claimed in claim 1, wherein the block includes a track groove extending along a groove axis parallel to the longitudinal axis of the sleeve and has a lateral opening intercommunicating with the track groove, wherein the track is slideably received in the track groove, wherein a cover is mounted to the block to cover the lateral opening of the block, and wherein the cover prevents the track from disengaging from the track groove.

3. The minimally invasive bone fracture positioning device as claimed in claim 2, wherein the track includes a first side having a first guiding groove and a second side spaced from the first side in a lateral direction perpendicular to the longitudinal axis of the sleeve and having a second guiding groove.

4. The minimally invasive bone fracture positioning device as claimed in claim 3, wherein the block includes a first protrusion slideably received in the first guiding groove, and wherein the cover includes a second protrusion slideably received in the second guiding groove.

5. The minimally invasive bone fracture positioning device as claimed in claim 1, further comprising an operating rod including a front end extending out of the sleeve via the alignment portion.

6. The minimally invasive bone fracture positioning device as claimed in claim 5, further comprising a drilling member removably mounted to the front end of the operating rod.

7. The minimally invasive bone fracture positioning device as claimed in claim 5, wherein the front end of the operating rod is configured for detachable attachment of a bone nail to be implanted into a pre-drilled bone.

8. The minimally invasive bone fracture positioning device as claimed in claim 1, further comprising a fixing hook fixed to an end of the track, and wherein the positioning portion is disposed on a distal end of the fixing hook.

9. The minimally invasive bone fracture positioning device as claimed in claim 8, wherein the fixing hook is C-shaped, G-shaped, J-shaped, L-shaped, or U-shaped, and wherein the positioning portion is in a form of a hook, a claw, or a collar.

10. The minimally invasive bone fracture positioning device as claimed in claim 1, wherein the track includes a measurement portion in a form of a scale on a surface of the track.

11. The minimally invasive bone fracture positioning device as claimed in claim 1, wherein the block includes a first engaging portion, wherein the support includes a second engaging portion, and wherein the first engaging portion and the second engaging portion have correspondingly formed engagement grooves.

* * * * *